(12) United States Patent
Metz

(10) Patent No.: US 11,931,916 B2
(45) Date of Patent: Mar. 19, 2024

(54) REPAIR DEVICE, AND METHOD FOR REPAIRING A DEFECT IN A WOODEN WORKPIECE

(71) Applicant: Fill Gesellschaft m.b.H., Gurten (AT)

(72) Inventor: Karl Metz, Eitzing (AT)

(73) Assignee: Fill Gesellschaft m.b.H., Gurten (AT)

( * ) Notice: Subject to any disclaimer, the term of this patent is extended or adjusted under 35 U.S.C. 154(b) by 915 days.

(21) Appl. No.: 16/963,059

(22) PCT Filed: Feb. 7, 2019

(86) PCT No.: PCT/AT2019/060047
§ 371 (c)(1),
(2) Date: Jul. 17, 2020

(87) PCT Pub. No.: WO2019/153027
PCT Pub. Date: Aug. 15, 2019

(65) Prior Publication Data
US 2020/0346361 A1  Nov. 5, 2020

(30) Foreign Application Priority Data
Feb. 9, 2018  (AT) .............................. A 50126/2018

(51) Int. Cl.
*B27G 1/00* (2006.01)
*G01N 21/898* (2006.01)
*G01N 33/46* (2006.01)

(52) U.S. Cl.
CPC ........... *B27G 1/00* (2013.01); *G01N 21/8986* (2013.01); *G01N 33/46* (2013.01)

(58) Field of Classification Search
CPC ...... B27G 1/00; G01N 21/8986; G01N 33/46; B27M 1/04
USPC ......................................................... 144/330
See application file for complete search history.

(56) References Cited

U.S. PATENT DOCUMENTS 2,392,751 A   1/1946  Mackenzie
3,405,746 A  10/1968  Skoog

FOREIGN PATENT DOCUMENTS

| AT | 397368 B | 3/1994 |
|---|---|---|
| DE | 3403248 A1 | 8/1985 |
| DE | 3531875 A1 | 3/1987 |
| DE | 8525512 * | 7/1987 |
| DE | 8525512.2 U1 | 7/1987 |
| EP | 1792696 A1 | 6/2007 |
| EP | 1982808 B1 | 1/2012 |

* cited by examiner

*Primary Examiner* — Jimmy T Nguyen
*Assistant Examiner* — Smith Oberto Bapthelus
(74) *Attorney, Agent, or Firm* — Stoel Rives LLP

(57) ABSTRACT

A repair device for repairing a defect in a wooden workpiece includes: a setting punch for inserting a repair patch into a recess formed in a wooden workpiece; a feed device for feeding the repair patches to the setting punch; and a detector for detecting the orientation of the repair patch with the aid of a marking arranged on the repair patch. A rotary device may be used for rotating the repair patch about a rotational axis. The detector may include a first sensor and a second sensor, which are arranged at the repair device in such a way that they are used for detecting the marking of detection regions disposed at a distance from one another, the marking being arranged on the repair patch.

17 Claims, 7 Drawing Sheets

REPAIR DEVICE, AND METHOD FOR REPAIRING A DEFECT IN A WOODEN WORKPIECE

RELATED APPLICATIONS

This application is a national stage under 35 U.S.C. § 371 of International Application No. PCT/AT2019/060047, filed Feb. 7, 2019, which claims priority of Austrian Patent Application No. A50126/2018, filed Feb. 9, 2018.

TECHNICAL FIELD

The field of the present disclosure relates to a repair device for repairing a defect in a wooden workpiece and to a method for repairing a defect in a wooden workpiece by using a repair device.

BACKGROUND

AT397368B discloses a device for patching up defects in wooden boards having a substantially longitudinal grain direction and a magazine housing for circular wooden discs having a grain direction substantially parallel to their end faces. Moreover, it may be provided that the discs comprise color markings used for their orientation when they are inserted into the defects.

EP1792696A1 discloses a device for patching up defects in wooden boards having a substantially longitudinal grain direction and a magazine housing for circular wooden discs having a grain direction substantially parallel to their end faces. Moreover, it may be provided that the discs comprise color markings used for their orientation when they are inserted into the defects.

The devices known from AT397368B and EP1792696A1 have the disadvantage that the markings of the wooden discs are only vaguely discernible. Thus, reliable alignment of the wooden discs is not ensured.

From EP1982808B1, a device configured for repairing defects in a wooden workpiece is known. The device is configured as a multi-axis robot and comprises a robot head, wherein the robot head comprises a milling tool and a magazine for patches, in particular wooden patches. The device further comprises means for pressing-in the patch, which means are formed by the robot head and/or the robot.

A need remains for an improved device and an improved method for aligning the repair patches.

SUMMARY

According to the present disclosure, a repair device for repairing a defect in a wooden workpiece includes: a setting punch for inserting a repair patch into a defect formed in the wooden workpiece; a feed device for feeding the repair patches to the setting punch; and a detection means for detecting the orientation of the repair patch with the aid of a marking arranged on the repair patch. In addition, a rotary device is provided, which is used for rotating the repair patch about a rotational axis. The detection means comprises a first sensor and a second sensor, which are arranged at the repair device in such a way that they are used for detecting the marking of detection regions disposed at a distance from one another, the marking being arranged on the repair patch.

The repair device according to the present disclosure has the advantage that the repair patches may be orientated with increased accuracy and at the same time also with increased speed, and the efficiency of the repair device may thus be increased. In particular, by means of the improved repair device, susceptibility to errors is simultaneously reduced; this way, the quality of the wooden workpieces repaired with the repair device may be simultaneously improved. In particular, using two sensors has the advantage that the marking is clearly discernible as such and possible variations of colors of the wooden patch do not result in incorrect orientation of the wooden patch.

It may further be appropriate if the rotary device comprises a rotatable setting punch, which is rotatable together with the repair patch. This has the advantage that the repair patch does not need to be rotated relative to the setting punch, but that the repair patch is rotated together with the setting punch and highly accurate angular alignment of the repair patch is thus facilitated.

It may further be provided that the rotary device comprises a gear wheel arranged at the rotatable setting punch, which gear wheel is coupled, by means of a traction means, with a pinion arranged at a rotary drive. By means of such coupling of the rotary drive with the setting punch, a highly accurate angular positioning of the setting punch may be achieved.

Furthermore, it may be provided that the rotary drive is configured as a servomotor. The advantage is that with a servomotor, a faster rotation process of the setting punch is facilitated, and high angular accuracy is simultaneously achieved during positioning.

An embodiment is also advantageous according to which it may be provided that the setting punch comprises a patch receiving surface, which is impingeable with negative pressure. With this measure, the repair patch may be received at the setting punch easily and without any additional aids.

According to a further development, it is possible that the setting punch is shiftable in the axial direction of the rotational axis by means of an activation actuator, in particular a pneumatic cylinder. A pneumatic cylinder has the advantage that the setting punch may be adjusted with high axial velocity, and at the same time, the compressive force acting upon the repair patch may be better predetermined or adjusted.

Moreover, it may be appropriate if the detection means is positioned relative to the setting punch in such a way that a bottom side of the repair patch is detectable. This has the advantage that the bottom side of the repair patch may be marked. This way, the marking is no longer visible after the repair patch has been inserted, and the wooden workpiece does not have to be reworked.

In addition, it may be provided that the first sensor and the second sensor are configured as an optical detection means, in particular as a laser sensor. Especially a marking detectable with optical sensors may be easily applied on the repair patch.

It may further be provided that a hollow-cylindrical holding-down punch is provided, wherein the setting punch is aligned coaxially to the holding-down punch and received within the cavity of the holding-down punch, wherein the holding-down punch is prestressed, by means of a spring element, in the axial direction towards the patch receiving surface of the holding-down punch, so that it projects above the setting punch in the rest state, and a receiving space for the repair patch is formed. By means of the holding-down punch, the wooden workpiece may be held in its position during insertion of the repair patch.

Furthermore, a method for repairing a defect in a wooden workpiece by using a repair device is provided. The method comprises the method steps of:

feeding a repair patch to a setting punch;

rotating the repair patch about a rotational axis while simultaneously detecting, by means of a detection means, a repair patch surface having a marking, wherein the marking indicates the grain direction of the repair patch. Moreover, a first sensor and a second sensor of the detection means detect the repair patch surface at two detection regions disposed at a distance from one another, wherein the grain direction of the repair patch may be determined when both sensors detect the marking arranged on the repair patch.

With the method according to the present disclosure, errors in the orientation of the repair patches may largely be prevented; this way, the repair device may be improved.

According to an advantageous further development, it may be provided that the sensors of the detection means are arranged at the repair device in such a way that after the marking has been detected, the repair patch is further rotated by a predetermined angle range until the final position of the repair patch has been reached. With this measure, it may be achieved that the rotational movement of the repair patch does not have to be stopped abruptly when the marking is detected, but that a certain period of continued movement is available, during which the rotational movement may be stopped.

In particular, it may be advantageous if the marking is arranged on a bottom side of the repair patch.

It may further be provided that the marking is arranged on the repair patch in parallel to the grain direction. This has the advantage that the marking may be applied on the blank patch even before the repair patch is cut out. For this purpose, a marking device may be run along the grain direction of the repair patch for marking the blank repair patch. With the described measure, the individual repair patches do not need to be provided with a marking.

In addition, it may be provided that the marking is applied on the repair patch in the form of a line running across the bottom side of the repair patch, in particular by means of an ink-jet printer.

In an alternative version, it may also be provided that the marking is applied on the repair patch in the form of a luminescent color, which is only visible when viewed under a UV lamp, for example.

An embodiment is also advantageous according to which it may be provided that the marking is applied to the repair patch before the latter is cut out from a blank patch. With the described measure, the individual repair patches do not need to be provided with a marking, but the blank patch may be marked in one work step in a time-saving manner.

According to a further development, it is possible that the detection regions of the sensors are diametrically opposed with respect to the rotational axis. This has the advantage that with this measure, it may be additionally checked whether the marking is correctly applied to the repair patch and whether the repair patch is centrally arranged at the setting punch.

In another variation, it may also be provided that the sensors or their detection regions are not diametrically opposed but arranged offset to one another at an angle. In this regard, the detection of the marking by means of the sensors is carried out in a time-delayed or angularly offset manner. In this regard, the correct angular position may be calculated.

It may further be provided that the setting punch is shifted relative to a machine frame for being positioned above the defect in a wooden workpiece.

In addition, it may be provided that the wooden workpiece is shifted relative to a machine frame. In this regard, the setting punch may be synchronized with the shifting of the wooden workpiece.

It may further be provided that on the bottom side of the repair patch, a layer is arranged, on which the marking is applied. Said layer may be formed by paper, cardboard or a veneer, for example.

BRIEF DESCRIPTION OF THE DRAWINGS

For better understanding of the invention, embodiments are explained in detail with reference to the following figures.

The following is shown in highly simplified, schematic representation.

DETAILED DESCRIPTION

First of all, it should be noted that in the embodiments described in different ways, identical parts are given identical reference numbers or identical component names, and the disclosures contained in the entire description may be correspondingly applied to identical parts with identical reference numbers or identical component names. Moreover, the position indications used in the description, such as at the top, at the bottom, lateral, etc. directly refer to the figure shown and described, and, if a position changes, said position indications are to be correspondingly applied to the new position.

Figure 1:
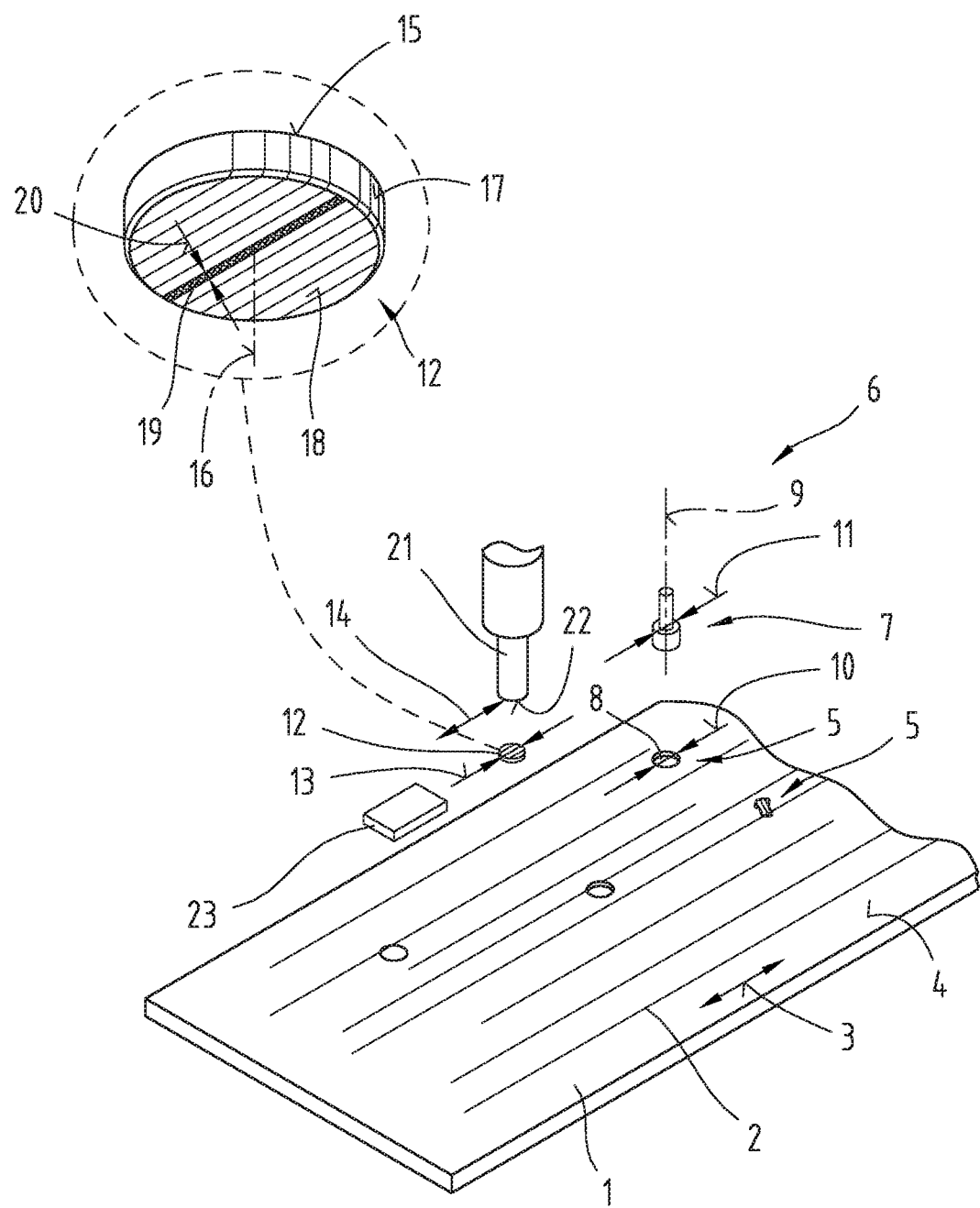
FIG. 1 a first embodiment of a repair device.

FIG. 1 shows a schematic representation of a wooden workpiece 1 comprising grains 2, which are arranged in a grain direction 3. The grains 2 or the grain direction 3 of the wooden workpiece 1 are particularly clearly visible on a surface 4 of the wooden workpiece 1. As wood is a natural material, defects 5 may also appear on the surface 4 of the wooden workpiece 1, which stand out visually from the rest of the surface 4 of the wooden workpiece 1. Such defects 5 are often undesirable and therefore have to be repaired.

The present disclosure relates to a repair device 6, a basic representation of which is shown in FIG. 1.

As can be seen from FIG. 1, it may be provided that in a first method step, the defects 5 are milled out with a milling cutter 7; this way, a recess 8 is formed in the surface 4 of the wooden workpiece 1. In particular, it may be provided that the recess 8 is configured as a blind hole. It may further also be provided that the recess 8 is configured as a clearance hole.

In particular, it may be provided that for creating the recess 8, the milling cutter 7 is only shifted along its milling cutter axis 9; this way, a diameter 10 of the recess 8 gets the same size as a diameter 11 of the milling cutter 7.

In the alternative, the milling cutter 7 may also be guided about the milling cutter axis 9 in a circular motion, so that a diameter 10 of the recess 8 is larger than the diameter 11 of the milling cutter 7.

In another method step, a repair patch 12 is inserted into the recess 8 by means of the repair device 6. The repair patch 12 has a diameter 13, which is adapted to the diameter 10 of the recess 8 in accordance with manufacturing tolerances; this way, the repair patch 12 may be received in the recess 8. It may further also be provided that the repair patch 12 and/or the recess 8 are tapered.

The repair patch 12 also comprises grains 2, which are arranged in a grain direction 14 of the repair patch 12. The grain direction 14 of the repair patch 12 is clearly visible on a surface 15 of the repair patch 12. In the built-in state of the repair patch 12, it is desirable that the surface 15 of the repair patch 12 and the surface 4 of the wooden workpiece 1 form an optically homogenous surface. Therefore, the grain direction 14 of the repair patch 12 must correspond to the grain direction 3 of the wooden workpiece 1. This may be achieved by the measures according to the present disclosure.

In order to be insertable into the recess 8, the repair patch 12 is cylindrical.

For better representation, the repair patch 12 is shown enlarged in a detailed view in FIG. 1, wherein the repair patch 12 is shown from a different perspective. As can be seen from this detailed view, the repair patch 12 is rotationally symmetric about a central axis 16, wherein the central axis 16 coaxially surrounds a shell surface 17. A bottom side 18 is arranged opposite of the surface 15 of the repair patch 12. On the bottom side 18 of the repair patch 12, the grains 2 may also be visible.

As can be further seen from the detailed view, it may be provided that on the bottom side 18 of the repair patch 12, a marking 19 is applied, by means of which the grain direction 14 of the repair patch 12 may be marked or determined afterwards. The marking 19 is preferably already applied on the repair patch 12 during its manufacturing.

As can be seen from the detailed view in FIG. 1, it may be provided that the marking 19 has the shape of a line applied on the bottom side 18 of the repair patch 12. In this regard, the marking 19 preferably runs exactly through the central axis 16 of the repair patch 12. In this regard, a width 20 of the marking 19 is selected to be as small as possible; however, it is selected to be large enough for the marking 19 to be subsequently detectable for aligning the repair patch 12.

In one embodiment, it may be provided that the marking 19 is applied on the bottom side 18 of the repair patch 12 by means of an ink-jet printer, for example. Of course, other known means for applying the marking 19 on the bottom side 18 of the repair patch 12 may be used as well. For example, it may be provided that the marking 19 is burned into the bottom side 18 of the repair patch 12 by means of a laser.

The repair patches 12 may, for example, be cut out from a blank repair patch by means of a crown milling cutter. In particular, it may be provided that the marking 19 is applied on the bottom side 18 of the repair patch 12 before the repair patch 12 is cut out from the blank patch.

Furthermore, a setting punch 21 is schematically shown in FIG. 1, which is used for inserting or pressing the repair patch 12 into the recess 8. In this regard, the punch 21 comprises a patch receiving surface 22, which is in contact with the surface 15 of the repair patch 12 at least while the repair patch 12 is pressed into the recess 8.

In FIG. 1, a feed device 23 is also schematically shown, by means of which the repair patches 12 may be fed to the setting punch 21. Alternatively, the repair patches 12 may also be taken by means of the setting punch 21 from a supply position.

In particular, it may be provided that the setting punch 21 is shiftable relative to the machine frame and thus relative to the wooden workpiece 1. It may further also be provided that the wooden workpiece 1 is also shiftable relative to the machine frame. This way, the required shifting path of the setting punch 21 may be kept as short as possible.

In a first embodiment, it may be provided that the milling cutter 7 and the setting punch 21 are arranged at a joint processing head and may be jointly shifted relative to the machine frame. This way, the position accuracy of the milling cutter 7 relative to the setting punch 21 may be increased.

In another embodiment, it may also be provided that the milling cutter 7 and the setting punch 21 may be shifted independently of each another relative to the machine frame. This way, the processing time may be reduced as the milling cutter 7 and the setting punch 21 may be operated in parallel and independently of each other.

Figure 2:
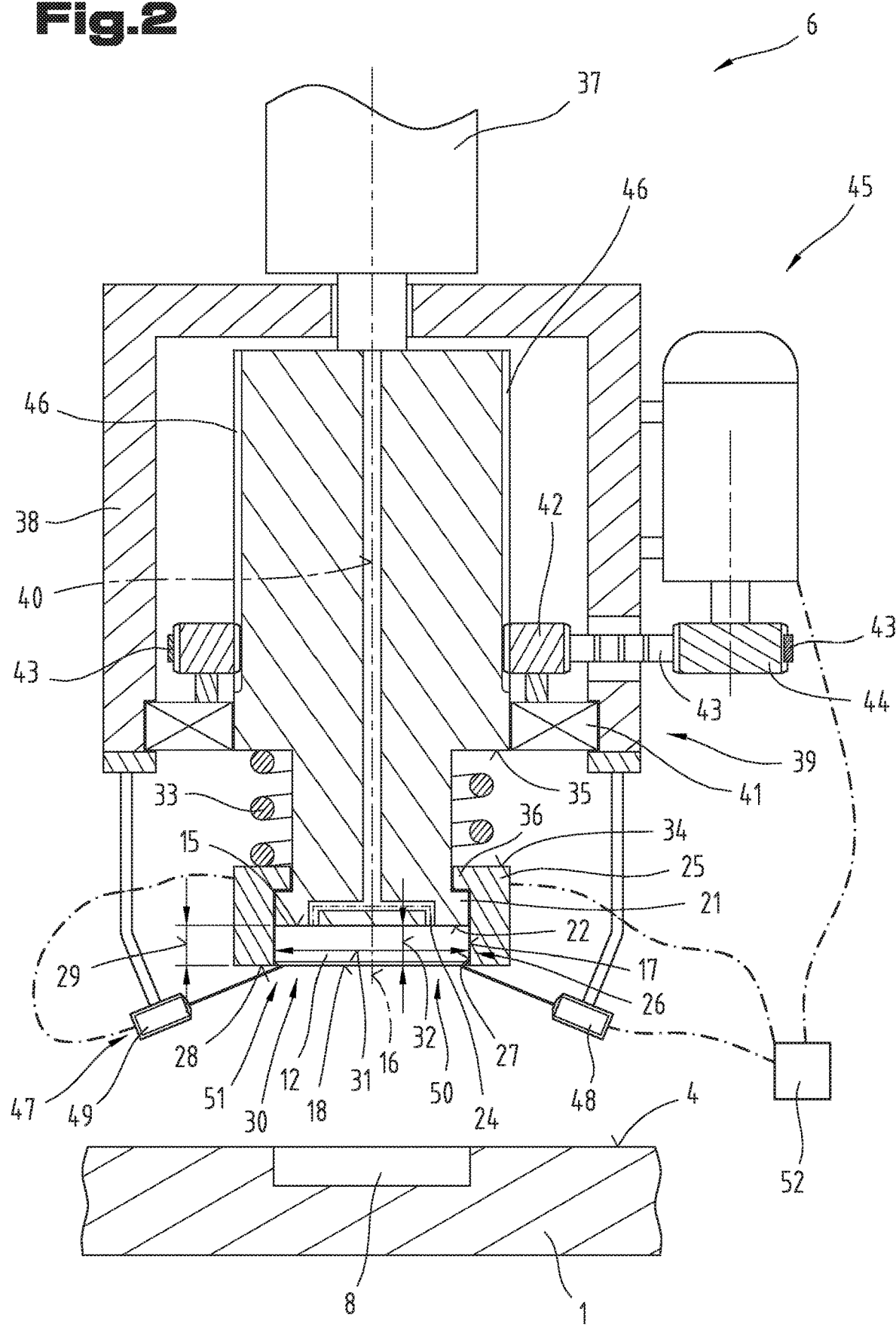
FIG. 2 a first embodiment of a setting punch in a receiving position.

FIG. 2 shows a schematic representation of an embodiment of the repair device 6, wherein the setting punch 21 in particular is shown in a sectional view. In this regard, the setting punch 21 is positioned above the surface 4 of the wooden workpiece 1 and has already received a repair patch 12. In this regard, the surface 15 of the repair patch 12 is in contact with the patch receiving surface 22 of the setting punch 21.

For being able to hold the repair patch 12 at the setting punch 21, it may be provided that the patch receiving surface 22 comprises negative-pressure bores 24, by means of which negative pressure may be applied to the patch receiving surface 22, whereby the repair patch 12 is sucked to the patch receiving surface 22.

As can be further seen from FIG. 2, it may be provided that a holding-down punch 25 is provided, which has a hollow-cylindrical shape and coaxially surrounds the setting punch 21 at least in the front region of the latter. The holding-down punch 25 comprises a cavity 26, in which the setting punch 21 is received. The cavity 26 comprises an inner shell surface 27, which is in contact with the setting punch 21 or guided along it. It may further be provided that in the starting position shown, a pressing surface 28 of the holding-down punch 25 protrudes over the patch receiving surface 22 of the setting punch 21 by a protrusion 29. This way, a receiving space 30 may be formed, in which the repair patch 12 may be received. The receiving space 30 is limited by the inner shell surface 27 of the holding-down punch 25 and the patch receiving surface 22 of the setting punch 21.

In particular, it may be provided that a diameter 31 of the inner shell surface 27 of the holding-down punch 25 is slightly larger than the diameter 13 of the repair patch 12. This way, it may be achieved that the repair patch 12 may be smoothly received in the receiving space 30. It may further be provided that the protrusion 29 is of approximately the same size as a patch height 32.

It may further be provided that the holding-down punch 25 is prestressed by means of a spring element 33 in the direction of the surface 4 of the wooden workpiece 1 and shiftable against the prestressing of the spring element 33 relative to the setting punch 21 when a force is applied to the pressing surface 28. In particular, it may be provided that the spring element 33 is arranged between the setting punch 21 and the holding-down punch 25 or is propped against the latter. For example, it may be provided that a supporting surface 34, which is in contact with the spring element 33, is arranged at the holding-down punch 25 opposite of the pressing surface 28. In addition, a supporting surface 35 facing the supporting surface 34 of the holding-down punch 25 may also be provided at the setting punch 21. Thus, the spring element 33 may extend between the supporting surface 34 of the holding-down punch 25 and the supporting surface 35 of the setting punch 21.

As can be seen from FIG. 2, the holding-down punch 25 may be arranged at the setting punch 21 in such a way that it is shiftable relative to the setting punch 21 in the axial direction. In addition, a stop element 36 may be provided, which limits the axial shifting of the holding-down punch 25 relative to the setting punch 21 in the direction of the surface 4 of the wooden workpiece 1. The positioning of the stop element 36 determines the value of the protrusion 29.

As can be seen from the embodiment in FIG. 2, it may be provided that the stop element 36 is configured as a step.

To be able to apply a shown holding-down punch 25 to the setting punch 21, it may be provided that the holding-down punch 25 is divided in two halves along a center plane, which are held together by means of fastening means.

Alternatively, it may be provided that the setting punch 21 comprises a head part, which may be connected with the main part by means of a fastening element, wherein the step is formed between the head part and the main part.

Moreover, an activation actuator 37 may be provided, by means of which the setting punch 21 may be shifted in the axial direction towards the wooden workpiece 1. In particular, it may be provided that a setting punch bracket 38 is formed, which is used for receiving or guiding the setting punch 21. The activation actuator 37 may be configured as a pneumatic cylinder, for example. The pneumatic cylinder may be fastened to the setting punch bracket 38, wherein a piston rod of the pneumatic cylinder may be coupled with the setting punch 21. With this measure, the setting punch 21 may be shifted relative to the setting punch bracket 38 in the axial direction.

Instead of a pneumatic cylinder, other activation actuators 37 may be used as well. It may further be provided that the setting punch bracket 38 and the setting punch 21 are configured as a cylinder/piston combination.

The repair device 6 further comprises a rotary device 39, by means of which the repair patch 12 is rotatable relative to the wooden workpiece 1. This way, the grain direction 14 of the repair patch 12 may be adapted to the grain direction 3 of the wooden workpiece 1. The rotary device 39 rotates the repair patch 12 about a rotational axis 40. Ideally, the repair patch 12 is received in the repair device 6 in such a way that the rotational axis 40 of the rotary device 39 and the central axis 16 of the repair patch 12 are positioned coaxially to one another. This way, the repair patch 12 may be rotated about its central axis 16 by means of the rotary device 39.

In the present embodiment, the rotary device 39 is configured in such a way that the setting punch 21 is rotatable, together with the repair patches 12 received thereon, relative to the setting punch bracket 38 and thus relative to the wooden workpiece 1. The rotary device 39 may comprise a bearing 41, by means of which the setting punch 21 is mounted at the latter rotatably about the rotational axis 40 relative to the setting punch bracket 38. The bearing 41 may be configured both as a rotary bearing and an axial bearing, by means of which the setting punch 21 is received at the setting punch bracket 38 such that it is both rotatable about the rotational axis 40 and shiftable along the rotational axis 40 in the axial direction.

For example, it may be provided that the bearing 41 is configured as a sliding bearing, by means of which the described movements are facilitated.

The rotary device 39 may further comprise a gear wheel 42, which may be coupled with a pinion 44 by means of a traction means 43. The pinion 44 may be arranged at a rotary drive 45, by means of which the rotation of the setting punch 21 about the rotational axis 40 may be initiated.

As can be seen from FIG. 2, it may be provided that the rotary drive 45 is coupled with the setting punch bracket 38 or arranged at the latter. The rotary drive 45 may be configured as an electric motor, in particular a servomotor, for example.

The traction means 43 may be configured as a toothed belt, for example. It is also conceivable that, for example, a chain or another traction means is used for transmitting force between the gear wheel 42 and the pinion 44.

In another embodiment, it is also conceivable that the pinion 44 directly engages with the gear wheel 42 without the interposed traction means 43.

In yet another variation, it is also conceivable that the gear wheel 42 is integrally formed in the setting punch 21, and the pinion 44 directly engages with the latter. In such a variation, axial shifting between the setting punch 21 and the pinion 44 may be directly compensated. Of course, it is also conceivable that the rotary drive 45 is coupled with the setting punch 21 via another torque connection.

In the present embodiment according to FIG. 2, the gear wheel 42 is rotatably received at the setting punch bracket 38 by means of the bearing 41. It may further be provided that within the setting punch 21, one or multiple drive slots 46 are provided, with which the gear wheel 42 engages. By means of the drive slots 46, the setting punch 21 is shiftable relative to the gear wheel 42 in the axial direction, with the torque connection being preserved at any time.

Instead of the drive slot 46, another torque connection shiftable in the axial direction may be provided as well, such as a microserration, a polygonal connection or other positive connections.

In addition, a detection means 47 is provided, which is used for detecting the angular position of the repair patch 12 by means of the marking 19. The detection means 47 comprises a first sensor 48 and a second sensor 49, which are configured for observing the bottom side 18 of the repair patch 12 in a first detection region 50 and in a second detection region 51.

The exact procedure for detecting the angular position is explained below with reference to FIGS. 3a to 3c.

The first sensor 48 and the second sensor 49 are also coupled with the setting punch bracket 38. Thus, the repair patch 12 is rotatable relative to the first sensor 48 or the second sensor 49 by means of the rotary drive 45.

As can be seen from FIG. 2, it may be provided that the two sensors 48, 49 are diametrically opposed with respect to the setting punch 21. The first sensor 48 or the second sensor 49 and the rotary drive 45 are coupled with a controller 52, by means of which the movement of the rotary drive 45 may be controlled. This way, the repair patch 12 may be aligned precisely with respect to its angular position.

As can be seen from FIG. 2, the first sensor 48 and the second sensor 49 are arranged below the setting punch 21 such that the bottom side 18 of the repair patch 12 is detectable by means of the sensors 48, 49.

In a first embodiment, it may be provided that the marking 19 is configured as a color marking and that the sensors 48, 49 are configured as optical sensors for detecting the color marking.

In another variation, it may also be provided that the marking 19 contains, for example, magnetic or magnetizable particles and that the sensors 48, 49 are configured as induction sensors, for example.

Figure 3A:
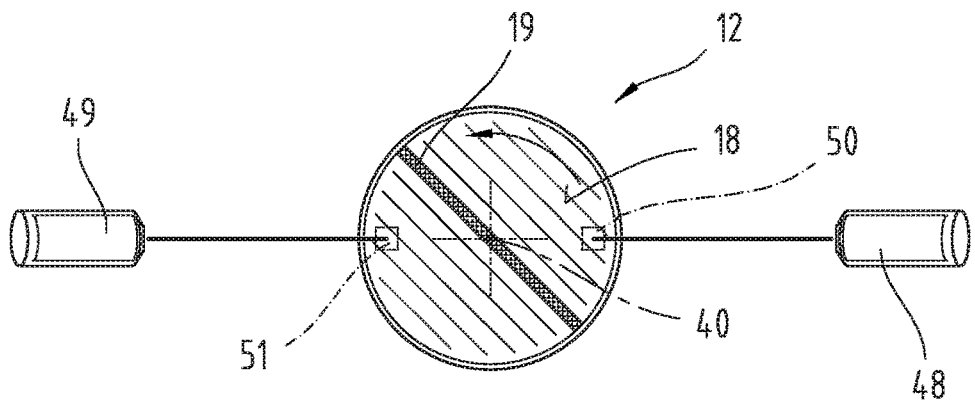
FIG. 3 a method sequence for aligning a repair patch.
Figure 3B:
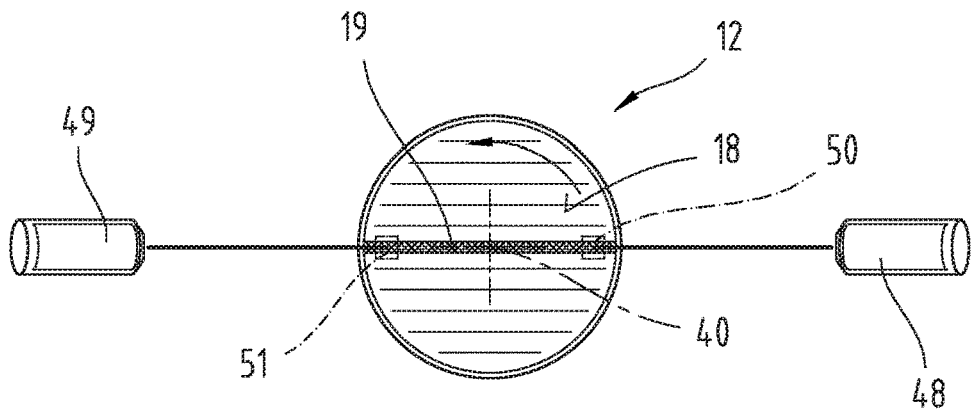
Figure 3C:
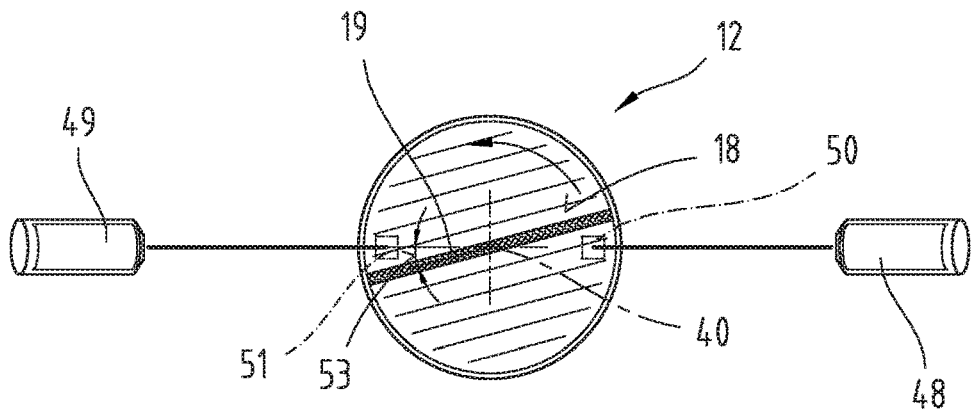

With reference to FIGS. 3a to 3c, the alignment and the correct angular rotation of the repair patch 12 are described. For describing the method sequence, in FIGS. 3a to 3c, bottom views of the repair device 6 and the repair patch 12 are shown, and a plan view of the bottom side 18 of the repair patch 12.

As can be seen from FIG. 3a, the repair patch 12 may be received in the repair device 6 arbitrarily. Subsequently, the repair patch 12 is rotated about the rotational axis 40 by means of the rotary device 39, wherein the first sensor 48 and the second sensor 49 detect two diametrically opposed detection regions 50, 51 and examine whether they contain the marking 19.

Only when the marking 19—as shown in FIG. 3b—is aligned such that the marking 19 is simultaneously detected in both detection regions 50, 51, the current angular position of the grain direction 14 of the repair patch 12 may be determined by means of the controller 52.

Figure 9:
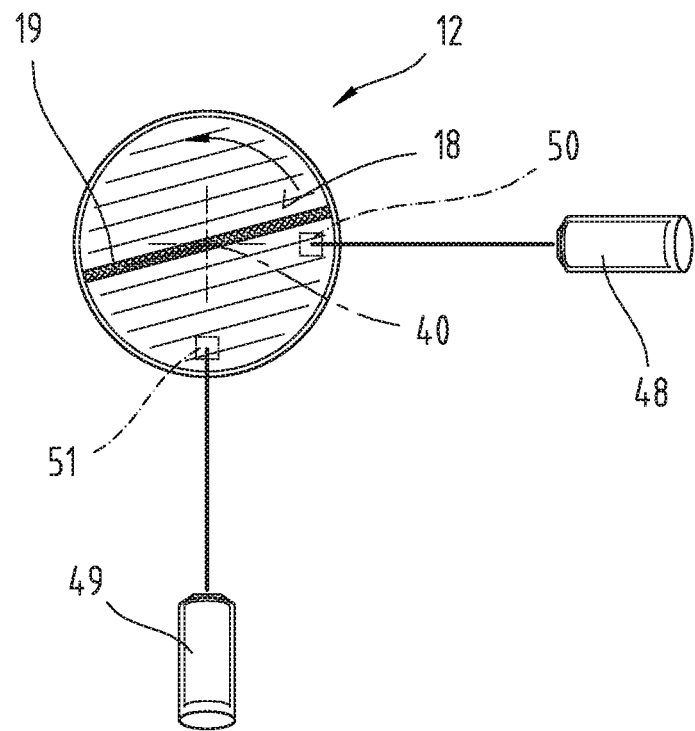
FIG. 9 another embodiment of the arrangement of the sensors.

Alternatively, as shown in FIG. 9, it may also be provided that the marking 19 is aligned or that the two detection regions 50, 51 are arranged such that the marking 19 is not simultaneously detected in the two detection regions 50, 51, but that the marking 19 is first detected in a first one of the detection regions 50, 51 and only detected in a second one of the detection regions 50, 51 after a certain angular rotation. In this process, the alignment of the repair patch 12 may also be ascertained.

In order not to have to abruptly stop the rotation process for aligning the repair patch 12, it may be provided that the marking 19 is arranged relative to the grain direction 14 of the repair patch 12 such that the correct angular position of the repair patch 12 relative to the wooden workpiece 1 is only achieved in a subsequent rotational angle 53, which is offset to the detection position according to FIG. 3b. In this regard, the size of the subsequent rotational angle 53 is selected such that the decelerating forces occurring due to the mass inertia of the setting punch 21 for stopping the rotational movement of the setting punch 21 are not too strong. The subsequent rotational angle 53 may, for example, be between 1° and 90°, in particular between 20° and 60°, preferably between 40° and 50°.

Detection of the current rotational angle of the repair patch 12 by means of at least two sensors 48, 49 has the advantage that any color defects on the bottom side 18 of the repair patch 12 or an incorrect position of the marking 19 or an incorrect positioning of the repair patch 12 at the setting punch is not erroneously recognized as a correct position of the repair patch 12.

Figure 4A:
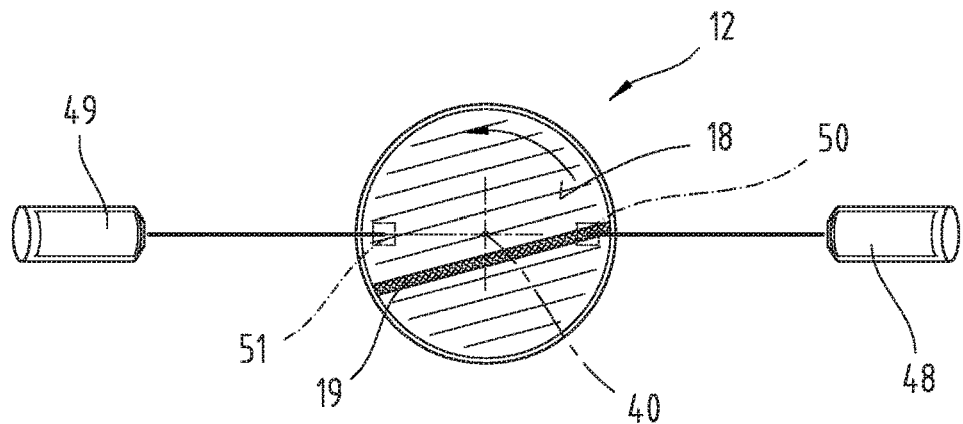
FIG. 4 representations of possible flaws in repair patches.
Figure 4B:
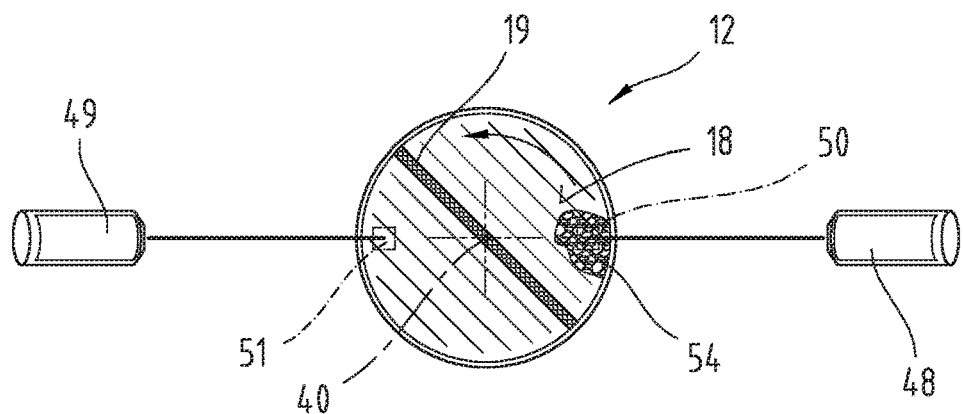

Such errors are shown in FIGS. 4a and 4b, for example. It can be seen from FIG. 4a that an eccentrical position of the marking 19 or an eccentrical arrangement of the repair patch 12 results in the corresponding repair patch 12 being eliminated since the correct position cannot be determined as described above. If the correct positioning of the repair patch 12 is not detected after an angular rotation of 360° at the latest, a corresponding command for eliminating the repair patch 12 is given in the controller 52.

Another embodiment illustrating the advantages of two sensors 48, 49 can be found in FIG. 4b. As can be seen from FIG. 4b, on the bottom side 18 of the repair patch 12, color stains 54 may occur, for example, which erroneously cannot be distinguished by the sensors 48, 49 from the marking 19. However, as can be seen from FIG. 4b, due to the duplication of the two sensors 48, 49, it may be detected that the correct angular position has not yet been reached, but that such a color stain 54 is detected and that the repair patch 12 therefore has to be rotated further until the marking 19 is simultaneously detected by both sensors 48, 49.

In the embodiment according to FIG. 3, the marking 19 is configured as a continuous line.

Figure 5A:
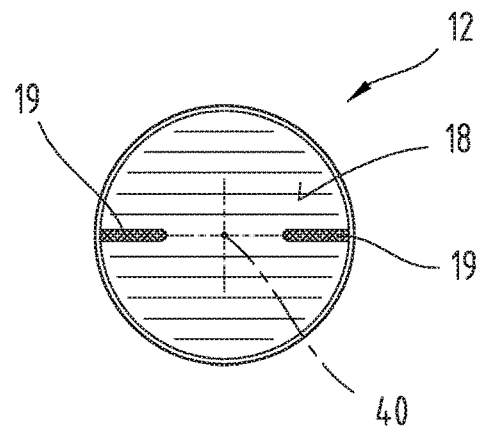
FIG. 5 representations of possible types of markings on repair patches.

In FIGS. 5a and b, further possible variations of the marking 19 are shown. As can be seen from FIG. 5a, it may be provided that the marking 19 is configured as a divided line.

Figure 5B:
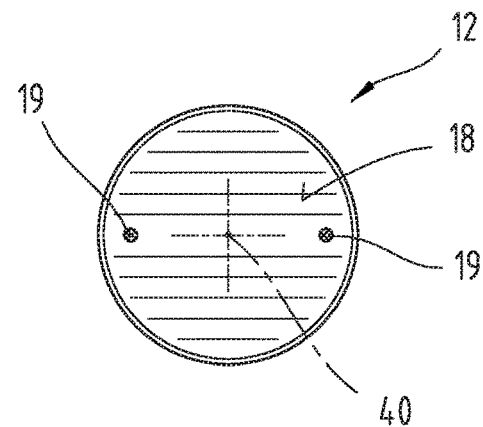

As can be seen from FIG. 5b, it may be provided that the marking 19 is formed by multiple dots, for example.

However, it is important that in the correct position of the repair patch 12, the marking 19 may be detected in both detection regions 50, 51.

Figure 6:
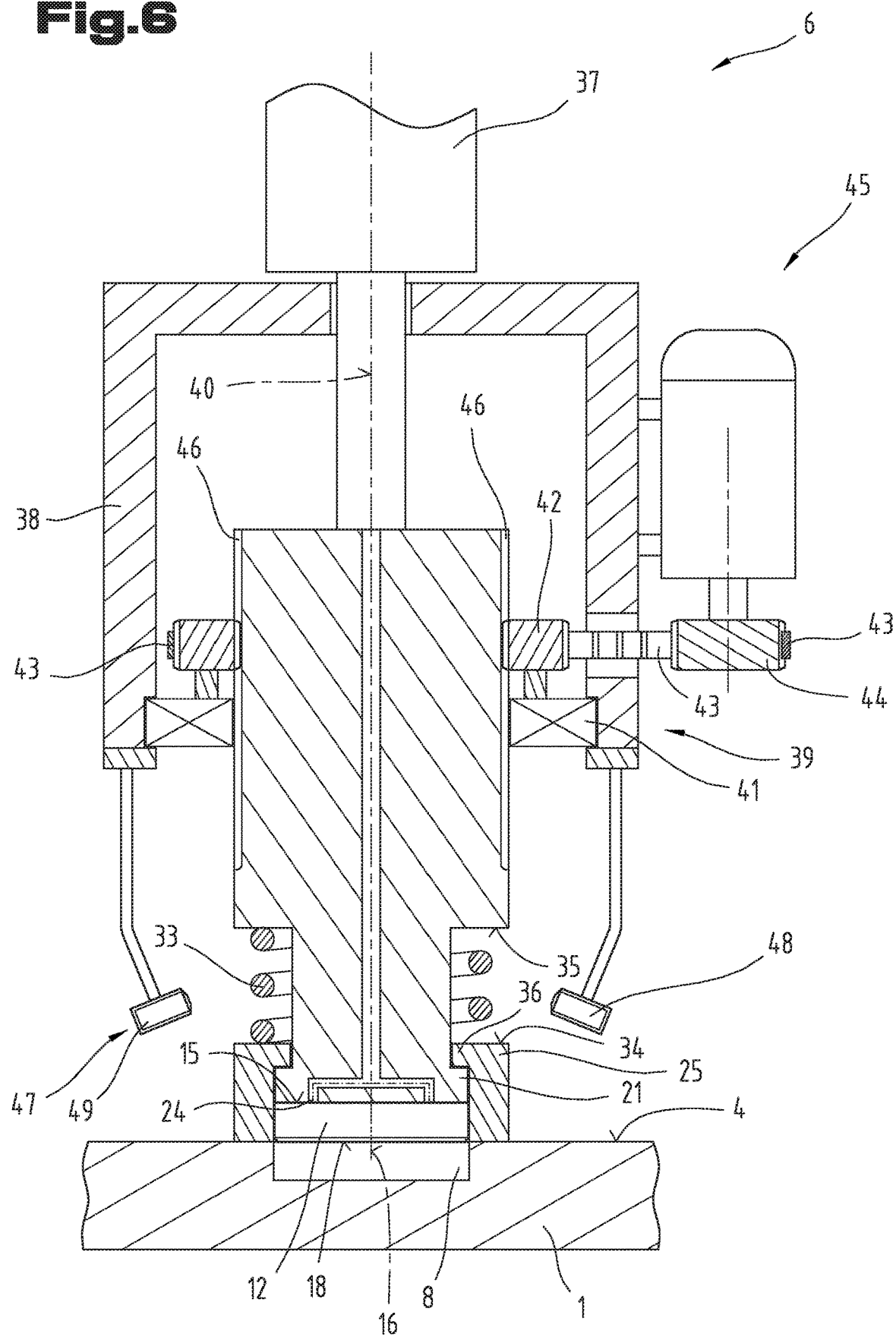
FIG. 6 the first embodiment of the setting punch in a lowered position.
Figure 7:
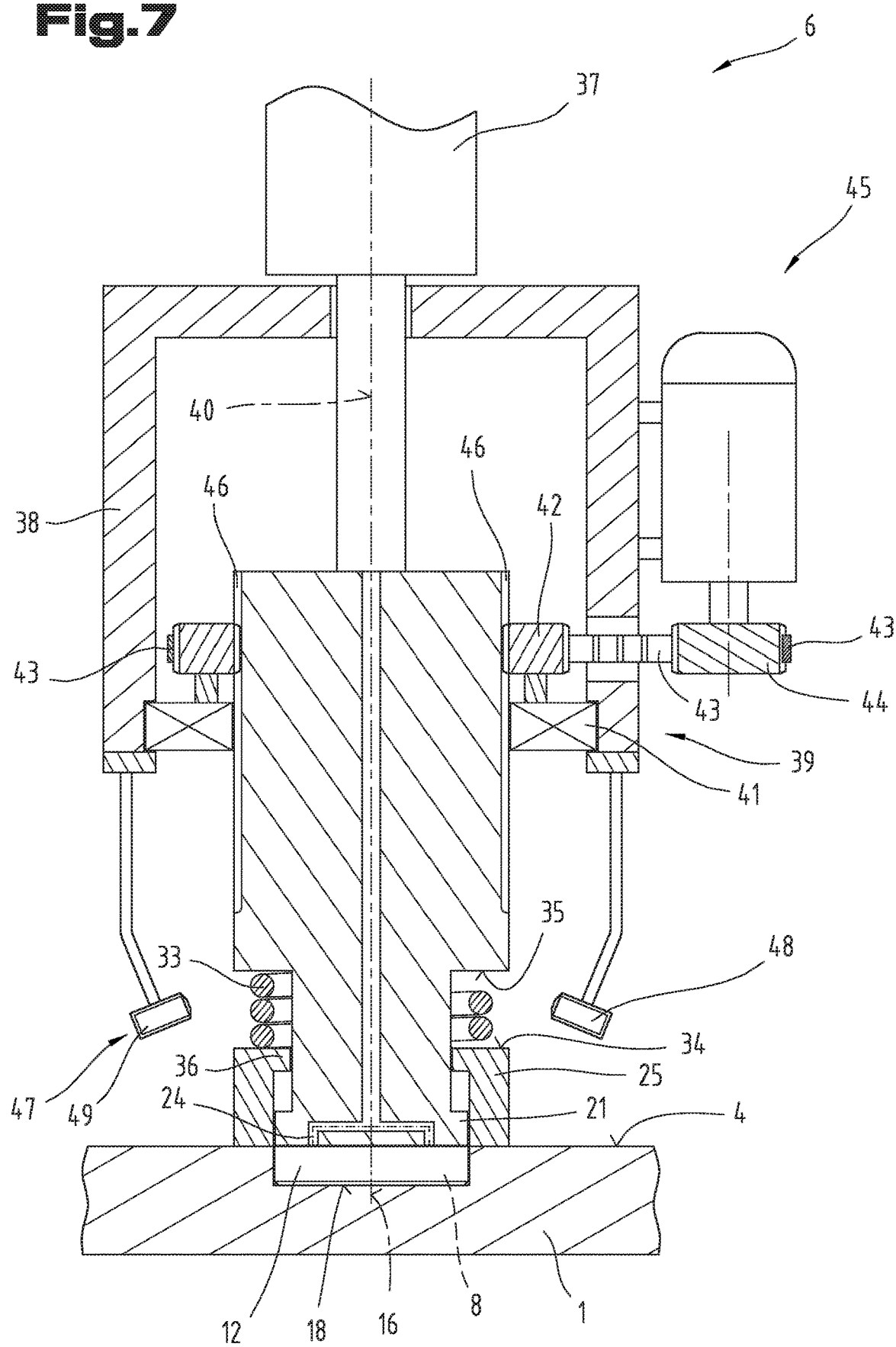
FIG. 7 the first embodiment of the setting punch in a lowered position.

In FIGS. 6 and 7, further method steps for inserting the repair patch 12 into the recess 8 are shown, wherein identical reference numbers or component names as in preceding FIG. 2 are again used for identical parts. To avoid unnecessary repetition, reference is made to the detailed description in preceding FIG. 2.

The method steps according to FIG. 6 are performed subsequently to the correct rotational alignment of the repair patch 12.

As can be seen from FIG. 6, the setting punch 21 is shifted in the axial direction towards the wooden workpiece 1 by means of the activation actuator 37, wherein, according to FIG. 6, the holding-down punch 25 initially rests on the wooden workpiece 1 and, during the further feed movement of the setting punch 21, is pressed against the wooden workpiece 1 by means of the spring force of the spring element 33. The setting punch 21 is further shifted towards the wooden workpiece 1 relative to the holding-down punch 25 until, according to the view in FIG. 7, the repair patch 12 has been inserted into the recess 8.

In further method steps, which are not shown, the setting punch 21 is moved upwards again by means of the activation actuator 37, and a new repair patch 12 is inserted into the receiving space 30.

In another embodiment, which is not shown, it may also be provided that no holding-down punch 25 surrounds the setting punch 21.

Figure 8:
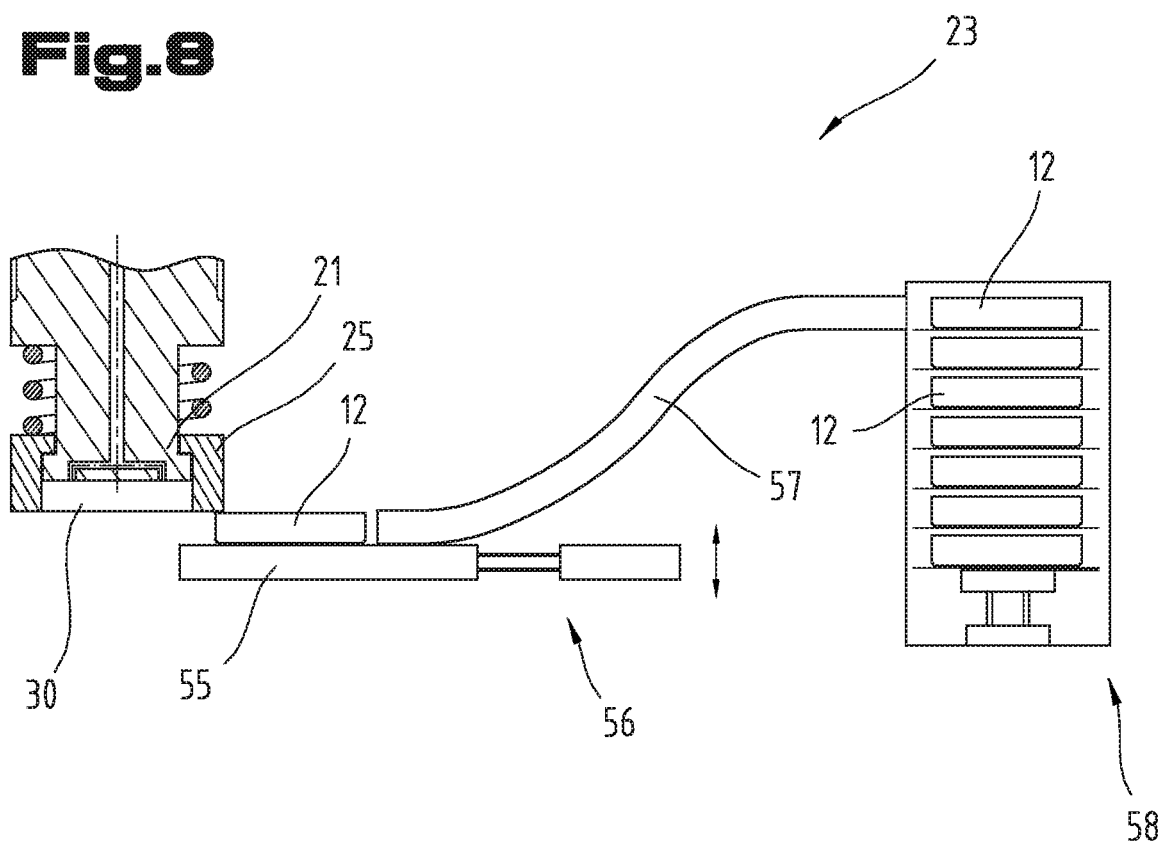
FIG. 8 a schematic representation of a repair device with a feed device for the repair patches.

FIG. 8 shows a schematic representation of the feed device 23, wherein identical reference numbers or component names as in the preceding figures are again used for identical parts. To avoid unnecessary repetition, reference is made to the detailed description in the preceding figures.

As can be seen from FIG. 8, the feed device 23 may comprise a manipulator 55, by means of which the repair patches 12 may be inserted into the receiving space 30. The manipulator 55 may be coupled with corresponding actuators 56 for moving the manipulator 55. It may further be provided that for feeding the repair patches 12 to the manipulator 55, a conveying hose 57 is provided, in which the repair patches 12 may be conveyed from a patch reservoir 58 to the manipulator 55, for example by means of compressed air.

FIG. 9 shows another embodiment of the arrangement of sensors 48, 49 in a schematic representation. As can be seen from FIG. 9, it may be provided that the sensors 48, 49 are not diametrically opposed at the setting punch 21, but that they are arranged at the setting punch 21 offset to one another at an angle, for example 90°. In this regard, the marking 19 is first detected by a first one of the sensors 48, 49. Only after a certain angular rotation of the repair patch 12 is the marking 19 detected by a second one of the sensors 48, 49. In this regard, with the knowledge of the position of the sensors 48, 49 or the angular rotation carried out between the two detections, the correct angular position of the repair patch 12 may be determined.

The embodiments show possible variations; however, it should be noted at this point that the present disclosure is not limited to its variations specifically shown; rather, various combinations of the individual variations are possible, and this variation possibility based on the technical teaching of the present disclosure is subject to the skills of the person skilled in the art active in this technical field.

The scope of protection is determined by the claims. However, the description and the drawings are to be used for construing the claims. The individual features or feature combinations of the different embodiments shown and described may constitute independent inventive solutions. A solution may be gathered from the description.

All indications of ranges of values in the present description are to be understood such that they also include any and all sub-ranges therefrom; for example, the indication 1 to 10 is to be understood such that all sub-ranges are included, starting at the lower limit 1 up to the upper limit 10; i.e. all sub-ranges start with a lower limit of 1 or larger and end at an upper limit of 10 or less, e.g. 1 to 1.7, or 3.2 to 8.1, or 5.5 to 10.

As a matter of form, it should finally be noted that for better understanding of the structure, some of the elements have been represented unscaled and/or enlarged and/or in reduced size.

The invention claimed is:

1. A repair device for repairing a defect in a wooden workpiece, said device comprising:
    a setting punch for inserting a repair patch into a recess formed in the wooden workpiece;
    a feed device for feeding the repair patch to the setting punch;
    a detector for detecting an orientation of the repair patch with the aid of a marking arranged on the repair patch; and
    a rotary device operable to rotate the repair patch about a rotational axis, and
    wherein the detector includes a first sensor and a second sensor, which are arranged for detecting the marking at a first detection region and a second detection region disposed at a distance from one another.

2. The repair device according to claim 1, wherein the rotary device comprises a gear wheel arranged at the setting punch, wherein the gear wheel is coupled, by a traction device, with a pinion arranged at a rotary drive.

3. The repair device according to claim 2, wherein the rotary drive is configured as a servomotor.

4. The repair device according to claim 1, wherein the setting punch comprises a patch receiving surface, which is impingeable with a negative pressure.

5. The repair device according to claim 1, wherein the setting punch is shiftable in an axial direction of the rotational axis by an activation actuator, wherein the activation actuator is a pneumatic cylinder.

6. The repair device according to claim 1, wherein the detector is positioned relative to the setting punch such that a bottom side of the repair patch is detectable.

7. The repair device according to claim 1, wherein the first sensor and the second sensor are configured as an optical detector, wherein the optical detector is a laser sensor.

8. The repair device according to claim 1, wherein a hollow-cylindrical holding-down punch is provided, wherein the setting punch is aligned coaxially to the holding-down punch and received within a cavity of the holding-down punch, wherein the holding-down punch is prestressed, by a spring element, in an axial direction towards a patch receiving surface of the holding-down punch, so that the holding-down punch projects above the setting punch in a rest state, and a receiving space for the repair patch is formed.

9. A method for repairing a defect in a wooden workpiece by using a repair device, the method comprising:
    feeding a repair patch to a setting punch;
    rotating the repair patch about a rotational axis while simultaneously detecting, by a detector, a surface of the repair patch, said surface having a marking that indicates a grain direction of the repair patch, wherein a first sensor of the detector detects the surface of the repair patch at a first detection region and a second sensor of the detector detects the surface of the repair patch at a second detection region, wherein the first and second detection regions are disposed at a distance from one another, wherein the grain direction of the repair patch is determined when the first sensor and the second sensor both detect the marking arranged on the repair patch.

10. The method according to claim 9, wherein the first sensor and the second sensor of the detector are arranged at the repair device in such a way that after the marking has been detected, the repair patch is further rotated by a predetermined angle range until a final position of the repair patch has been reached.

11. The method according to claim 9, wherein the marking is arranged on a bottom side of the repair patch.

12. The method according to claim 9, wherein the marking is arranged on the repair patch in parallel to the grain direction.

13. The method according to claim 9, wherein the marking is applied on the repair patch in the form of a line running across a bottom side of the repair patch an ink-jet printer.

14. The method according to claim 13, wherein the marking is applied to the repair patch before the repair patch is cut out from a blank patch.

15. The method according to claim 14, wherein the first detection region of the first sensor and the second detection region of the second sensor are diametrically opposed with respect to the rotational axis.

16. The method according to claim 9, wherein the setting punch is shifted relative to a machine frame for being positioned above the defect in the wooden workpiece.

17. The method according to claim 9, wherein the wooden workpiece is shifted relative to a machine frame.

* * * * *